United States Patent
Hedman

(10) Patent No.: US 8,211,938 B2
(45) Date of Patent: Jul. 3, 2012

(54) DIRECT APPLICATION OF NON-TOXIC CROSSLINKING REAGENTS TO RESIST PROGRESSIVE SPINAL DEGENERATION AND DEFORMITY

(75) Inventor: Thomas P. Hedman, Stevenson Ranch, CA (US)

(73) Assignee: Orthopeutics, L.P., Lexington, KY (US)

( * ) Notice: Subject to any disclaimer, the term of this patent is extended or adjusted under 35 U.S.C. 154(b) by 251 days.

(21) Appl. No.: 12/715,737

(22) Filed: Mar. 2, 2010

(65) Prior Publication Data

US 2010/0158887 A1 Jun. 24, 2010

Related U.S. Application Data

(60) Division of application No. 11/712,684, filed on Feb. 28, 2007, now Pat. No. 8,022,101, which is a continuation-in-part of application No. 11/346,464, filed on Feb. 2, 2006, which is a continuation-in-part of application No. 10/786,861, filed on Feb. 24, 2004, now Pat. No. 7,435,722, which is a continuation-in-part of application No. 10/230,671, filed on Aug. 29, 2002.

(60) Provisional application No. 60/498,790, filed on Aug. 28, 2003, provisional application No. 60/316,287, filed on Aug. 31, 2001.

(51) Int. Cl.
- A61K 31/352 (2006.01)
- A61K 31/353 (2006.01)
- A61K 38/45 (2006.01)
- A61K 38/44 (2006.01)
- A61K 31/7004 (2006.01)
- A61K 31/121 (2006.01)
- C07D 311/00 (2006.01)

(52) U.S. Cl. ...................................................... 514/456
(58) Field of Classification Search .................. 514/456, 514/23, 125, 638; 424/94.5, 94.4; 549/399, 549/406

See application file for complete search history.

(56) References Cited

U.S. PATENT DOCUMENTS

| | | | |
|---|---|---|---|
| 6,165,489 A | 12/2000 | Berg et al. | |
| 6,719,797 B1 | 4/2004 | Ferree | |
| 6,812,211 B2 * | 11/2004 | Slivka et al. | 424/94.4 |
| 2004/0010251 A1 | 1/2004 | Pitaru et al. | |

* cited by examiner

Primary Examiner — Rosanne Kosson
(74) Attorney, Agent, or Firm — Berliner & Associates

(57) ABSTRACT

A method of treatment of native, non-denatured tissue to increase resistance to tearing, fissuring, rupturing, and/or delamination, comprising the step of: contacting at least a portion of the tissue with an effective amount of a reagent that increases crosslinks in the tissue.

13 Claims, 2 Drawing Sheets

DIRECT APPLICATION OF NON-TOXIC CROSSLINKING REAGENTS TO RESIST PROGRESSIVE SPINAL DEGENERATION AND DEFORMITY

CROSS-REFERENCE TO RELATED APPLICATIONS

This application is a divisional application of application Ser. No. 11/712,684, filed on Feb. 28, 2007, now U.S. Pat. No. 8,022,101, which is a continuation-in-part of application Ser. No. 11/346,464, filed on Feb. 2, 2006, which is a continuation-in-part of application Ser. No. 10/786,861, filed on Feb. 24, 2004, now U.S. Pat. No. 7,435,722, which claims the benefit of U.S. Provisional Application Ser. No. 60/498,790, filed on Aug. 28, 2003, and which is a continuation-in-part of application Ser. No. 10/230,671, filed on Aug. 29, 2002, which claims the benefit of U.S. Provisional Application Ser. No. 60/316,287, filed on Aug. 31, 2001.

BACKGROUND OF THE INVENTION

1. Field of the Invention

The present invention relates to a method for treatment of tissue, for example, collagenous tissue, where a deleterious mechanical loading environment contributes to the degradation of the tissue. In various embodiments, the present invention relates to a method for treatment of load supporting fibrous tissues, such as degenerated intervertebral discs and surrounding tissues, degenerative knee meniscus, prevention of extrusion or expulsion of materials or devices implanted such as nucleus replacement or augmentation, to methods and devices to improve the resistance to tearing of the tissue and to prevent disc herniation, and to methods to improve fatigue resistance, to resist ongoing deforming forces and curve progression in scoliosis as well as other progressive spinal deformities, to non-toxic crosslinking reagents that are effective fatigue and tear inhibitors and joint stabilizers, and to methods and devices for improving the environment for biological activity in the central region of the disc by increasing the permeability or more specifically, the hydraulic and macromolecular permeability and diffusivity of the outer region of the disc.

2. Description of the Related Art

Deleterious mechanical loading environments contribute to the degradation of collagenous tissue in a variety of manners. For instance, fatigue is a weakening of a material due to repetitive applied stress. Fatigue failure is simply a failure where repetitive stresses have weakened a material such that it fails below the original ultimate stress level. In bone, two processes—biological repair and fatigue—are in opposition, and repair generally dominates. In the intervertebral disc, the prevalence of mechanical degradation of the posterior annulus (Osti 1992) suggests that fatigue is the dominant process. Active tissue response (adaptation, repair) does not play a strong role in the case of mature intervertebral disc annular material. The intervertebral disc is comprised of three parts: the nucleus pulposus (NP) or nucleus, the annulus fibrosus (AF) or annulus, and the cartilaginous endplates. The characteristic of the inner annulus and outer nucleus blend with ongoing degeneration, with the nucleus becoming more fibrous and decreasing in water content. Similarly, the boundary between outer nucleus and inner annulus is known to fade and becomes indistinct with ongoing degeneration. As a principally avascular structure, the disc relies on diffusion for nutrition of its limited number of cells. Age related changes interfere with diffusion presumably contributing to declining cell viability and biosynthetic function (Buckwalter et al. 1993, Buckwalter 1995). Age related decline in numbers of cells and cell functionality compromises the ability of the cells to repair mechanical damage to the matrix. Regeneration of the matrix in the nucleus following enzymatic degradation has been accomplished, albeit inconsistently (Deutman 1992). Regeneration of functional annular material has not yet been realized.

Combined with this limited potential for repair or regeneration, studies have shown that posterior intervertebral disc tissue is vulnerable to degradation and fatigue failure when subjected to non-traumatic, physiologic cyclic loads. Prior work has shown deterioration in elastic-plastic (Hedman 99) and viscoelastic (Hedman 00) material properties in posterior intervertebral disc tissue subjected to moderate physiological cyclic loading. Cyclic load magnitudes of 30% of ultimate tensile strength produced significant deterioration of material properties with as little as 2000 cycles. Green (1993) investigated the ultimate tensile strength and fatigue life of matched pairs of outer annulus specimens. They found that fatigue failure could occur in less than 10,000 cycles when the vertical tensile cyclic peak exceeded 45% of the ultimate tensile stress of the matched pair control. In addition, Panjabi et al (1996) found that single cycle sub-failure strains to anterior cruciate ligaments of the knee alter the elastic characteristics (load-deformation) of the ligament. Osti (1992) found that annular tears and fissures were predominantly found in the posterolateral regions of the discs. Adams (1982) demonstrated the propensity of slightly degenerated discs to prolapse posteriorly when hyperflexed and showed that fatigue failure might occur in lumbar discs as the outer posterior annulus is overstretched in the vertical direction while severely loaded in flexion. Disc prolapse involves tearing and fissuring of the annulus fibrosus or outer portion of the intervertebral disc with migration and extrusion of central, nucleus pulposus materials. In an analytical study, interlaminar shear stresses, which can produce delaminations, have been found to be highest in the posterolateral regions of the disc (Goel 1995). These prior data indicate: 1) the posterior disc and posterior longitudinal ligament are at risk of degenerative changes, and that 2) the mechanism of degeneration can involve flexion fatigue with possible fissuring, tearing and delamination.

A different type of mechanical degradation of collagenous tissue occurs in scoliosis and other progressive spinal deformities. Scoliosis refers to an abnormal lateral, primarily, or other curvature or deformity of the spine, often of unknown origin. Progressive spinal deformities can also occur subsequent to surgical bone removal, with or without accompanying spinal instrumentation, such as in a neural decompression procedure or subsequent to vertebral failure. The bony vertebral failure itself may occur as a result of trauma or of age related osteoporosis or osteopenia. Kyphotic deformity (loss of outward concavity or increase in outward convexity), in the lumbar spine also known as flat-back syndrome, is a frequent sequela to spinal fusion or installation of spinal instrumentation, especially in the case of a long, multi-level, surgical construct. Severe curvature and ongoing curve progression can lead to many other health disorders including but not limited to compromised respiratory function. In addition, one's lifestyle can be adversely affected and a loss of cosmesis can result. A large segment of the population is affected by scoliosis, approximately 2% of women and 0.5% of men. Over 80% of scoliosis is of no known origin (i.e., idiopathic). Approximately 80% of idiopathic scoliosis develops in young pubescent adults. The incidence of deformity increases with age. Existing conservative approaches to limit curve progression such as external bracing can be awkward or restricting, and are of disputed value. Surgical correction of severe curves can be intensive with a long recovery period, require the need for post-operative bracing, and be fraught with many other post-operative problems.

Another form of spinal deformity, spondylolisthesis commonly occurs in the lower lumbar region of the spine. Spondylolisthesis involves the slippage of one vertebral level relative to an adjacent level. Progressive listhesis leads to sciatica and pain. Surgical intervention is an option to prevent progressive slip, especially when the slip has reached a greater amount of slip displacement or slip angle. However, nonsurgical means of preventing a slip to progress to the point where surgery is indicated have not been available previously.

Current treatments for scoliosis and other progressive spinal deformities consist of bracing and surgery. The purpose of orthopaedic braces is to prevent increasing spinal deformity, not to correct existing deformity. Braces are generally used in children with an expected amount of skeletal growth remaining, who have curve magnitudes in the range of 25 to 40 degrees. External braces are routinely used as a standard of care. Yet there is controversy regarding the effectiveness of external bracing. The magnitude of forces delivered to the spine corresponding to brace loads applied to the torso cannot be quantified directly. Larger forces applied to the torso may also result in brace induced pathologies to the tissues in contact with the brace. Some studies suggest that braces are effective in halting curve progression in about 80 percent of afflicted children. But because the option to do nothing but observe curve progression is inappropriate, there is no generally accepted percentage of these curves that would stop progressing on their own or due to other factors.

Naturally occurring collagen crosslinks play an important role in stabilizing collagenous tissues and, in particular, the intervertebral disc. Significantly higher quantities of reducible (newly formed) crosslinks have been found on the convex sides than on the concave sides of scoliotic discs (Nuance, et al. 1998). Similarly, Greve, et al. (1988) found a statistically increased amount of reducible crosslinks in scoliotic chicken discs at the same time that curvatures were increasing. This suggests that there is some form of natural, cell-mediated crosslink augmentation that occurs in response to the elevated tensile environment on the convex side of scoliotic discs. Greve also found that there were fewer reducible crosslinks at the very early stages of development in the cartilage of scoliotic chickens. They concluded that differences in collagen crosslinking did not appear to be causative because there was not a smaller number of crosslinks at later stages of development. In fact, later on, when the scoliotic curve was progressing, there were statistically significant greater numbers of collagen crosslinks, perhaps in response to the curvature. Although not the conclusion of Greve, this can be interpreted as being a sufficient depletion of crosslinks in the developmental process with long enough duration to trigger the progression of scoliotic curvature that was later mended by a cellular response that produced higher than normal levels of crosslinks. These studies suggest that the presence of naturally occurring collagen crosslinks may be critical to prevent ongoing degradation and for mechanical stability of intervertebral disc tissue in scoliotic spines.

It is important to note that these studies did not quantify the integrity or crosslink quantities associated with the elastin and elastic fiber network which also plays a role in the mechanical integrity of these collagenous materials. Some of the benefit of crosslinking of the principally collagenous tissues like the intervertebral disc may also be attributed to an effect on the elastin and elastic fiber network and other proteins (such as link proteins) in these collagenous tissues. In the same way that intramolecular, intermolecular and interfibrillar crosslinks of collagen molecules and fibers benefit the tissue and joint mechanics, including resistance to degradation, tears and deformity, and increased permeability, intramolecular, intermolecular and interfibrillar crosslinks involving elastin and the elastic fiber network could provide benefits to the tissue and joint mechanics and nutrition. In fact, the same reagents effective at augmenting collagen crosslinking may also augment crosslinks involving the elastin and elastic fiber network, or other tissue proteins.

It is well documented that endogenous (naturally occurring—enzymatically derived and age increasing non-enzymatic) and exogenous collagen crosslinks increase the strength and stiffness of collagenous, load-supporting tissues (Wang 1994, Chachra 1996, Sung 1999a, Zeeman 1999, Chen 2001). Sung (1999b) found that a naturally occurring crosslinking agent, genipin, provided greater ultimate tensile strength and toughness when compared with other crosslinking reagents. Genipin also demonstrated significantly less cytotoxicity compared to other more commonly used crosslinking agents. With regard to viscoelastic properties. Lee (1989) found that aldehyde fixation reduced stress-relaxation and creep in bovine pericardium. Recently, naturally occurring collagen crosslinks were described as providing 'sacrificial bonds' that both protect tissue and dissipate energy (Thompson, et al. 2001). To date, there is no known reference in the literature as to the ability of exogenous crosslinks to decrease the viscoelastic characteristic of hysteresis or to increase the ability of the collagenous tissue to store enemy. A need therefore exists to find biochemical methods that enhance the body's own efforts to stabilize discs in scoliotic and other progressively deforming spines by increasing collagen crosslinks.

Mechanical degradation of collagenous tissue can also occur if the environment for biological activity in the central region of the disc is poor. Tissue engineering is a burgeoning field which aims to utilize cells, special proteins called cytokines and synthetic and native matrices or scaffolds in the repair and regeneration of degraded, injured or otherwise failed tissues. With regard to the intervertebral disc, biological solutions like tissue engineering are hindered by the harsh, hypoxic (oxygen deficient) avascular (very little if any direct blood supply) environment of moderately degenerated intervertebral discs. The disc is known to receive nutrients and discard cell waste products primarily by diurnal-cyclic pressure driven fluid flow and diffusion through the annulus fibrosus and through the cartilaginous endplates that connect the disc to the bony, well vascularized, spinal vertebrae. The disc cartilaginous endplates lose permeability by calcification while the disc itself becomes clogged up with an accumulation of degraded matrix molecules and cell waste products. This loss of disc permeability effectively reduces the flow of nutrients to the cells and the flow of waste products from the cells in the interior central region of the disc, the nucleus pulposus. This loss of flow of nutrition to the disc causes a loss of cell functionality, cell senescence, and causes a fall in pH levels that further compromises cell function and may cause cell death (Buckwalter 1995, Horner and Urban 2001). Horner and Urban showed that density of viable cells was regulated by nutritional constraints such that a decline in glucose supply led to a decrease in viable cells. Boyd-White and Williams (1996) showed that crosslinking of basement membranes increased permeability of the membranes to macromolecules such as serum albumin, crosslinked albumin, and a series of fluorescein isothiocyanate dextrans of four different molecular sizes. It is herein suggested, then, that increased crosslinking of the annulus fibrosus and/or the endplates of intervertebral discs, though very different and more complex collagenous tissues than basement membranes, would provide for increased flow of glucose and other nutritional macromolecules to cells and waste products from the cells in the interior region of the disc, thus improving their viability.

Intervertebral disc herniation involves fissuring, rupture or tearing of the annulus fibrosus followed by displacement of the central portion of the disc posteriorly or posterolaterally through the torn tissue. The deformed or displaced disc protrusion can compress a nerve root and/or the spinal cord. Clinical symptoms associated with herniated disc include back pain and radiculopathy including leg pain, sciatica and muscle weakness. Treatments for herniated disc commonly comprise excision of the protruding disc segment and other tissues suspected to be involved with nerve compression and pain. Prior to tearing through the outer annular fibers the disc can bulge posteriorly potentially applying pressure to neural elements. Approximately a decade typically separates the first, acute incidence of low back pain and the onset of radicular symptoms. There is currently no treatment available to prevent degeneration, annular tearing, nucleus migration, herniation and sciatica.

Similarly, emerging nucleus augmentation or replacement technologies rely on the integrity of a surgically weakened annulus fibrosus to prevent migration and extrusion or expulsion of implanted materials or devices. These materials and devices are typically targeted for patients in the early stages of disc degeneration (Galante I-III), where there is less degradation of the annulus fibrosus because of the reliance on annulus integrity for the success of these implants. However the annulus is typically compromised further in order to implant these materials and devices to the central region of the disc. Clinical data at this time suggests that implant migration and extrusion is one of the main complications to this type of treatment. High rates of extrusion have been reported for some nucleus replacements. 10% for the device with the most clinical experience and 20-33% for another. A need therefore exists for a method for resisting annulus tearing after or at the same time of implantation of a nucleus augmentation or nucleus replacement devices. Normal physiological loading can displace, extrude or expulse devices and materials implanted into the center, nucleus region of the intervertebral disc. Consequently, a treatment capable of improving annulus tear resistance could be useful both to prevent eminent disc protrusions and as an adjunct to a disc augmentation or nucleus replacement procedure.

To date, no treatments capable of reducing mechanical degradation to native, non-denatured collagenous tissues currently exist. In fact, no other collagenous tissue fatigue inhibitors have been proposed. A need therefore exists for a method for improving the resistance of collagenous tissues in the human body to fatigue and for otherwise reducing the mechanical degradation of human collagenous tissues, in particular, the posterior annulus region of the intervertebral disc. In addition, a need exists to increase resistance to scoliotic curve progression and other progressive spinal deformities by treatment of appropriate regions on the tensile side (convex) of affected discs and to improve permeability, particularly the hydraulic and macromolecular permeability and diffusivity of the outer region of the disc, but also throughout the disc annulus in whole or in part and the cartilaginous endplates of the disc, the flow of nutrition, such as glucose and other nutritional macromolecules, to cells in the annulus and in the central portion of the disc, and the flow of waste products from the cells.

Spinal deformities following vertebral fractures including kyphotic deformities following vertebral compression fractures are sometimes treated by injecting a cement-like material into the intravertebral space (vertebroplasty) sometimes following a vertebral height restoration procedure to reduce the deformity (kyphoplasty). A complementary procedure to increase the tension band restraint by increasing and improving elastic characteristics of the tensile side of the affected discs would also be beneficial in preventing the incidence of deformity as well as the progression of the deformity. Improvement of the tension band characteristics in this way stabilizes the spinal column and is a means of internal, natural bracing.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, methods, devices, and application trays particularly pointed out in the appended claims.

SUMMARY OF THE INVENTION

It is one object of the present invention to provide a method of improving the resistance of native, non-denatured collagenous tissues in the human body to mechanical degradation by contacting the tissue with crosslinking reagents.

It is another object of the present invention to provide a method of curtailing the progressive mechanical degradation of intervertebral disc tissue by enhancing the body's own efforts to stabilize aging discs by increasing collagen crosslinks.

It is another object of the present invention to provide a method that uses crosslinking reagents with substantially less cytotoxicity compared to common aldehyde fixation agents in order to facilitate direct contact of these reagents to tissues in the living human body.

It is another object of the present invention to increase the crosslinking of non-denatured disc annular tissue by directly contacting living human disc tissue with appropriate concentrations of a non-toxic crosslinking reagent (or a mixture of crosslinking reagents) such as genipin (a geniposide) or proanthrocyanidin (a bioflavinoid).

It is another object of the present invention to provide a treatment method for minimally invasive delivery of the non-cytotoxic crosslinking reagent such as injections directly into the select tissue using a needle, for example into the convex side of discs involved in the curvature or potential curvature of the spine, or placement of a time-release delivery system such as a carrier gel or ointment, or a treated membrane or patch directly into or onto the target tissue.

It is another object of the present invention to a composition composed of non-toxic crosslinking renews that can be used as effective fatigue inhibitors.

in accordance with the present invention, there is provided a method for treatment of tissues where a deleterious mechanical loading environment contributes to the degradation of the tissue. The deleterious mechanical loading environment may consist of normal physiological repetitive loading, otherwise known as fatigue or normal sustained or postural loading known as creep, which is also typically repetitive in nature, and therefore a form of fatigue. The present invention provides a method for treatment of degenerated intervertebral discs to improve fatigue resistance. The present invention also provides non-toxic crosslinking compositions that are effective fatigue inhibitors.

The present invention uses non-cytotoxic crosslinking reagents such as genipin or proanthocyanidin, a bioflavinoid, or a sugar such as ribose or threose, or byproducts of metabolism and advanced glycation endproducts (AGES) such as glyoxal or methylglyoxyl or an enzyme such as lysyl oxidase (LO) enzyme (either in purified form or recombinant), or transglutaminase (Tgase), or a LO or Tgase promotor, or an epoxy or a carbodiimide to improve the stability of intervertebral discs in scoliotic or other mechanically insufficient or potentially deforming or deforming spines to eliminate or augment the need for external bracing. Preferably, the crosslinking reagent contains one of the following ranges of agent concentrations or a combination or agent concentrations: at least 0.001% (0.01 mg/ml) of human recombinant transglutaminase, at least 0.01% (0.1 mg/ml) of purified animal liver transglutaminase, at least 0.25% genipin, at least 0.1% proanthrocyanidin, at least 100 mM EDC, at least 100 mM ribose, at least 100 mM L-Threose, at least 50 mM methylglyoxal, at least 50 mM glyoxal, at least 0.001% lysyl oxidase in a 0.1 M urea solution. In the case of non-enzymatic agents such as ribose. L-Threose, methylglyoxal and glyoxal, the reagent will preferably contain an oxidant such as hydrogen peroxide, or sodium percarbonate, or sodium borate, or an amino acid hydroperoxide, or perborate, or a buffer such as sodium bicarbonate or phosphate, or some combination of oxidants and buffers. Further, the crosslinking reagent may include a crosslinking agent in a carrier medium.

A method of improving the resistance of collagenous tissue to mechanical degradation in accordance with the present invention comprises the step of contacting at least a portion of a collagenous tissue with an effective amount of crosslinking reagent. The collagenous tissue to be contacted with the crosslinking reagent is preferably a portion of an intervertebral disc or similar fibrous collagenous tissue such as knee meniscus. The contact between the tissue and the crosslinking reagent is effected by injections directly into the select tissue using a needle. Alternatively, contact between the tissue and the crosslinking reagent is effected by placement of a time-release delivery system such as a gel or ointment, or a treated membrane or patch directly into or onto the target tissue. Contact may also be effected by, for instance, soaking or spraying.

It is another object of the present invention to provide biochemical methods that enhance the body's own efforts to stabilize discs in scoliotic and mechanically insufficient spines by increasing collagen crosslinks.

It is another object of the present invention to cause this stability enhancement by reducing the bending hysteresis (energy lost in a complete loading-unloading cycle) which leaves an increased angle after a deforming force is applied to the deformed joint of scoliotic or mechanically insufficient spines, that is increasing the "bounce-back" characteristics from a deformity-increasing load by injecting non-toxic crosslinking reagents into the convex or tensile side of discs involved in the scoliotic curve or potential or progressing deformity.

It is another object of the present invention to cause this stability enhancement by increasing the bending elastic energy storage and return (elasticity) of scoliotic or mechanically insufficient or potentially deforming or deforming spines by injecting non-toxic crosslinking reagents into the convex side of discs involved in the potential or progressing deformity curve.

It is another object of the present invention to cause this stability enhancement by increasing the bending stiffness (resistance to the deformity-increasing bend) of scoliotic or mechanically insufficient or potentially deforming or deforming spines by injecting non-toxic crosslinking reagents into the convex side of discs involved in the potential or progressing deformity curve.

The less energy lost in deformity-increasing bending, or the less hysteresis in a bending cycle in the direction of increasing the existing or potential deformity, means that a greater amount of energy was stored and can be recovered in the form of immediate recovery of pre-bending shape. Greater hysteresis reflects a slower recovery of the pre-loaded shape and therefore a greater propensity for increasing the deforming moments on the deformed joint (deforming moments increase with increasing deformity) and, therefore, a greater propensity for increased deformity.

The appropriate locations for injection of the crosslinking reagent may be determined using three-dimensional reconstructions of the affected tissues as is possible by one skilled in the art, and combining these reconstructions with an algorithm to recommend the optimum placement of these reagents so as to affect the greatest possible restraint of potential or progressive deformity or ongoing scoliotic curve progression. These three-dimensional depictions of preferred locations for crosslinker application may best be created with custom computer software that incorporates any type of medical images of the patient that are available, and may best be displayed on a computer driven display device such as a lap-top computer or a devoted device. Additional, guidable, arthroscopic types of devices may be used, or developed or modified, to facilitate application of the reagents to appropriate areas on the intervertebral discs or adjacent bony, capsular or ligamentous tissues.

It is another object of the present invention to increase the permeability, particularly the hydraulic and macromolecular permeability and diffusivity, of the outer region of the intervertebral disc, the annulus fibrosus, and/or the cartilaginous endplates and by this improve the fluid and solute and suspended particulate flux to improve the flow of nutrition, such as glucose and other nutritional macromolecules, to cells in the annulus and in the central region, or nucleus pulposus, of an intervertebral disc, and the flow of waste products from the cells, by increasing collagen crosslinks.

It is another object of the present invention to increase the biological viability of cells in the central region of the intervertebral disc by increasing collagen crosslinks.

The present invention then also relates to a new use of the non-cytotoxic crosslinking reagent to improve the permeability of the outer regions of the intervertebral disc, possibly including the endplates, providing for an increased flux of fluids and solutes to and from the central region of the disc, thus improving the nutrition to the cells in this central region and the outflow of wasteproducts from this region. The collagenous tissue to be contacted with the crosslinking reagent is preferably a portion of an intervertebral disc or similar fibrous collagenous tissue such as knee meniscus. These reagents are preferably injected or otherwise applied to the majority of the outer annular regions of the intervertebral disc and to the endplates at the superior and inferior aspects of the disc. Additional, guidable, arthroscopic types of devices may be developed to facilitate application of the reagents to appropriate areas on the intervertebral discs.

It is another object of the present invention to increase the tear resistance of collagenous tissues such as the annulus fibrosus of the intervertebral disc and the knee meniscus, by increasing collagen crosslinks.

It is another object of the present invention to prevent expulsion or extrusion of disc nucleus materials or nucleus augmentation or replacement materials or devices by increasing resistance to tissue fissuring and tearing.

In accordance with the present invention, there is provided a method for treatment of tissues to increase resistance to tissue tearing. The present invention provides a method for treatment of degenerated intervertebral discs to resist disc herniation. The present invention also provides non-toxic crosslinking compositions that are effective tearing inhibitors. The present invention provides a method for resisting the migration or expulsion or extrusion of materials or devices implanted in the central nucleus region of intervertebral discs. The present invention also provides a method for treatment of knee meniscus to hinder or prevent tissue tearing.

A method of improving the resistance of collagenous tissue to tearing in accordance with the present invention comprises the step of contacting at least a portion of a collagenous tissue with an effective amount of the crosslinking reagent. The collagenous tissue to be contacted with the crosslinking reagent is preferably a portion of an intervertebral disc or similar fibrous collagenous tissue such as knee meniscus. The contact between the tissue and the crosslinking reagent is effected by injections directly into the select tissue using a needle. Alternatively, contact between the tissue and the crosslinking reagent is effected by placement of a time-release delivery system such as a gel or ointment, or a treated membrane or patch directly into or onto the target tissue. Contact may also be effected by, for instance, soaking or spraying.

DETAILED DESCRIPTION GE THE INVENTION

Figure 1:
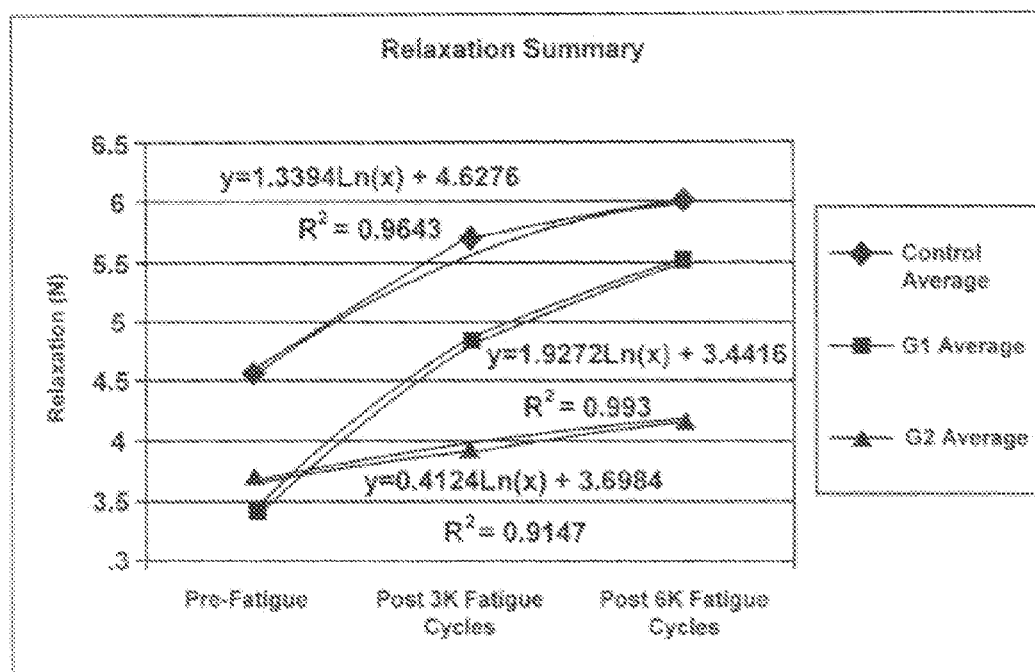
FIG. 1 is a graph of relaxation (N) v. numbers of cycles showing the effect of genipin crosslinking treatments (G1=0.033 g/mol, G2=0.33 g/mol) on posterior intervertebral disc stress relaxation.

The present invention provides a method of improving the resistance of collagenous tissues in the human body to mechanical degradation comprising the step of contacting at least a portion of a collagenous tissue with an effective amount of a crosslinking reagent. In one embodiment of the present invention, the method of the present invention also provides a method of curtailing the progressive mechanical degradation of intervertebral disc tissue by enhancing the body's own efforts to stabilize aging discs by increasing collagen crosslinks. In this embodiment, this mechanical degradation may be in response to physiologic levels of repetitive loading.

The crosslinking reagent of the present invention is not particularly limited. Any crosslinking reagent known to be substantially non-cytotoxic and to be an effective cross-linker of collagenous material may be used. The crosslinking reagent is required to be substantially non-cytotoxic in order to facilitate direct contact of the crosslinking agent to tissues in the living human body. Preferably, the crosslinking reagent exhibits substantially less cytotoxicity compared to common aldehyde fixation agents. More preferably, a non-cytotoxic crosslinking reagent is used.

Appropriate cytotoxicity testing will be used to verify the minimal cytotoxicity of candidate crosslinking reagents prior to use in humans. Tissue specific in vitro tests of cytotoxicity, of the standard form applied to mouse connective tissue (F895-84 (2001)e1 Standard Test Method for Agar Diffusion Cell Culture Screening for Cytotoxicity), or Chinese Hamster Ovaries (ASTM E1262-813 (1996) Standard Guide for Performance of the Chinese Hamster Ovary Cell/Hypoxanthine Guanine Phosphoribosyl Transferase Gene Mutation Assay) preferably utilizing cell lines from tissues approximating the fibrous and gelatinous tissues of the intervertebral disc, should be conducted to evaluate the level of toxicity of any specific combination of crosslinking reagents known to have minimal cytotoxicity. These in vitro tests should similarly be followed by in vivo animal tests prior to use in humans.

The crosslinking reagent includes at least one crosslinking agent. The crosslinking agent chosen in accordance with the present invention is an effective cross-linker of collagenous material. When used in a cross-linking reagent, an effective crosslinker is one that increases the number of crosslinks in the collagenous tissue when the crosslinker is brought into contact with a portion of the collagenous tissue. An effective crosslinker improves the fatigue resistance of the treated tissue, reduces material property degradation resulting from repetitive physiologic loading, increases resistance to tissue tearing, resists progressive deformity, increases hydraulic permeability of the tissue, or reduces the increase of viscoelastic properties of the treated tissue due to fatigue loading. Likewise, an effective crosslinker may reduce the decrease in elastic-plastic properties due to fatigue loading of the treated tissue.

In accordance with the invention, this method would utilize specific formulations of crosslinking, reagents with substantially less cytotoxicity compared to common aldehyde fixation agents in order to facilitate direct contact of these reagents to tissues in the living human body. Bioflavinoids and geniposides have been shown to be effective crosslinkers with minimal cytotoxicity. Similarly, sugar (e.g., ribose or threose) solutions and byproducts of metabolism and advanced glycation endproducts (AGEs) such as glyoxal or methylglyoxyl have been shown to increase the number of non-enzymatic glycation produced crosslinks (naturally produced crosslinks, pentosidine is one example). Lysyl oxidase is the naturally produced enzyme involved in the formation of immature and mature endogenous (naturally occurring) collagen crosslinks. The method used to increase the crosslinking of disc annular tissue may include directly contacting living human disc tissue with appropriate concentrations of minimally-cytotoxic crosslinking reagents such as genipin or proanthocyanidin, a bioflavinoid, or a sugar such as ribose or threose, or byproducts of metabolism and advanced glycation endproducts (AGEs) such as glyoxal or methylglyoxyl or an enzyme such as lysyl oxidase (LO) enzyme (either in purified form or recombinant), or transglutaminase (Tgase), or a LO or Tgase promotor, or an epoxy or a carbodiimide. Preferably, the crosslinking reagent contains one of the following ranges of agent concentrations or a combination of agent concentrations: at least 0.001% (0.01 mg/ml) of human recombinant transglutaminase, at least 0.01% (0.1 mg/ml) of purified animal liver transglutaminase, at least 0.25% genipin, at least 0.1% proanthrocyanidin, at least 100 mM EDC, at least 100 mM ribose, at least 100 mM L-Threose, at least 50 mM methylglyoxal, at least 50 mM glyoxal, at least 0.001% lysyl oxidase in a 0.1 M urea solution. In the case of non-enzymatic agents such as ribose, L-Threose, methylglyoxal and glyoxal, the reagent will preferably contain an oxidant such as hydrogen peroxide, or sodium percarbonate, or sodium borate, or an amino acid hydroperoxide, or perborate, or a buffer such as sodium bicarbonate or phosphate, or some combination of oxidants and buffers. More than one crosslinking agent may be used.

The crosslinking reagent may include a carrier medium in addition to the crosslinking agent. The crosslinking agent may be dissolved or suspended in the carrier medium to form the crosslinking reagent. In one embodiment, a crosslinking agent is dissolved in a non-cytotoxic and biocompatible carrier medium. The carrier medium is required to be substantially non-cytotoxic in order to mediate the contact of the crosslinking agent to tissues in the living human body without substantial damage to the tissue or surrounding tissue. Preferably, the carrier medium chosen is water, and more preferably, a saline solution. Preferably, the pH of the carrier medium is adjusted to be the same or similar to the healthy tissue environment. Even more preferably, the carrier medium is buffered. In one embodiment of the present invention, the carrier medium is a phosphate buffered saline (PBS).

When the crosslinking agent is dissolved in a carrier medium, the concentration of the crosslinking agent in the carrier medium is not particularly limited. The concentration may be in any amount effective to increase the crosslinking of the tissue while at the same time remaining substantially noncytotoxic.

In accordance with the present invention, the crosslinking reagent is brought into contact with a portion of a native, non-denatured collagenous tissue. As used herein, collagenous tissue is defined to be a structural or load supporting tissue in the body comprised of a substantial amount of collagen. Examples would include intervertebral disc, articular cartilage, meniscus, fibrocartilage, ligament, tendon, bone, and skin. In general, the portion of the collagenous tissue to be brought into contact with the crosslinking reagent is the portion of the tissue that is subject to loading. Further, where at least some degradation of the collagenous tissue has occurred, the portion of the tissue to be contacted with the crosslinking reagent is at least the portion of the tissue that has been degraded or deformed. Preferably, the entire portion that is subject to loading or the entire portion that is degraded or deformed is contacted with the crosslinking reagent. Further, the tissue adjacent the portion of collagenous tissue subject to the loading may also be contacted with the crosslinking reagent.

The collagenous tissues that are particularly susceptible for use in accordance with the present invention include intervertebral discs and articular cartilage or fibrocartilage such as knee meniscus. Where the collagenous tissue is an intervertebral disc, the portion of the intervertebral disc that is preferably contacted by the crosslinking reagent is the posterior and posterolateral annulus fibrosis.

The selected portion of the collagenous tissue must be contacted with an effective amount of the non-toxic crosslinking reagent. An "effective amount" is an amount of crosslinking reagent sufficient to have a mechanical effect on the portion of the tissue treated. Specifically, an "effective amount" of the crosslinking reagent is an amount sufficient to improve the fatigue resistance of the treated tissue, reduce material property degradation resulting from repetitive physiologic loading, increases resistance to tissue tearing, increases resistance to deforming forces, increases hydraulic permeability of the tissue, or reduce the increase of viscoelastic properties of the treated tissue due to fatigue loading, or reduce the decrease of elastic-plastic properties of the treated tissue due to fatigue loading. An effective amount may be determined in accordance with the viscoelastic testing, tear testing, deformity resistance testing, hydraulic permeability testing, and/or the elastic-plastic testing described herein with respect to Examples 1, 2, 3, 4 and 5.

The method of the present invention includes contacting at least a portion of the collagenous tissue with an effective amount of the crosslinking reagent. The contact may be effected in a number of ways. Preferably, the contacting of collagenous tissue is effected by a means for minimally invasive delivery of the non-cytotoxic crosslinking reagent. Preferably, the contact between the tissue and the crosslinking reagent is effected by injections directly into the select tissue using a needle. Preferably, the contact between the tissue and the crosslinking reagent is effected by injections from a single or minimum number of injection locations. Preferably, an amount of crosslinking solution is injected directly into the targeted tissue using a needle and a syringe. Preferably, a sufficient number of injections are made along the portion of the tissue to be treated so that complete coverage of the portion of the collagenous tissue to be treated is achieved.

Alternatively, contact between the tissue and the crosslinking reagent is effected by placement of a time-release delivery system directly into or onto the target tissue. One time-released delivery system that may be used is a treated membrane or patch. A reagent-containing patch may be rolled into a cylinder and inserted percutaneously through a cannula to the tissue sight, unrolled and using a biological adhesive or resorbable fixation device (sutures or tacks) be attached to the periphery of the targeted tissue.

Another time-released delivery system that may be used is a gel or ointment. A gel or ointment is a degradable, viscous carrier that may be applied to the exterior of the targeted tissue.

Contact also may be effected by soaking or spraying, such as intra-capsular soaking or spraying, in which an amount of crosslinking solutions could be injected into a capsular or synovial pouch.

A form of mechanical degradation of load supporting collagenous tissues includes tearing of the tissues. In a second embodiment, the present invention relates to methods and devices for the treatment of fibrous collagenous tissues and surrounding tissues by directly contacting the select tissues with a crosslinking reagent to improve the resistance to tearing of the tissue. The collagenous tissues that are particularly susceptible to tearing include intervertebral discs and articular cartilage or fibrocartilage such as knee meniscus. Where the collagenous tissue is an intervertebral disc, the portion of the intervertebral disc that is preferably contacted by the crosslinking reagent is the posterior and posterolateral annulus fibrosis. Where the treated tissues include the intervertebral disc, the present invention also relates to methods and devices for prevention of disc herniation. The present invention could be used in a conservative approach to prevent tearing of disc tissue, in particular, radial tearing of the annulus fibrosus leading to expulsion of nucleus pulposus materials.

One aspect of this embodiment provides a method of improving the tear resistance of native intervertebral disc tissue prior to a disc herniation by contacting the tissue with a non-toxic crosslinking reagent. This embodiment also provides a method of improving tear resistance where a herniation has already occurred by contacting the tissue with non-toxic crosslinking reagents. Another aspect of this embodiment provides a method of improving the tear resistance of native knee meniscus tissue subsequent to a partial tearing of the meniscus. This embodiment also provides a method of improving tear resistance of native knee meniscus tissues prior to tearing of the meniscus.

In this embodiment, an effective amount of crosslinking reagent is an amount that creates crosslinks in the target tissue, preferably in regions of the tissue where the majority of tissue tearing is known to occur. In the case of intervertebral disc tissues, the treatment is preferably on the posterior and posterolateral regions of the annulus fibrosus such that the resistance to tearing is increased for the prevention of disc herniation. In the case of knee meniscus tissues, the tissue is preferably treated in the region of existing partial tears and to surrounding meniscal tissues. The knee meniscal tissue is also preferably treated in its entirety. If only the medial meniscus or only the lateral meniscus is affected, both the medial and lateral meniscus can be treated. If the meniscal tissues in one knee is affected, the crosslinking treatment could also be made on the meniscal tissues in the contralateral knee.

Preferably, a method according to this embodiment uses a minimally invasive delivery of the non-cytotoxic crosslinking reagents, such as a series of injections, to the affected discs or knee meniscus or cartilaginous or bony or capsular or ligamentous tissues in order to contact the appropriate tissue with appropriate concentrations of non-toxic crosslinking reagents. This aspect of the present invention is used in a conservative approach to prevent ongoing tearing and degeneration of these tissues and in the case of the intervertebral disc, to prevent subsequent herniations of the disc.

Preferably, a treatment method according to this embodiment incorporates a means for minimally invasive delivery of the non-cytotoxic crosslinking reagent such as placement of a time-release delivery system such as an imbedded pellet or time release capsule, or a treated membrane or patch directly into or onto the target tissue. Additional, guidable, arthroscopic-types of devices may be developed to facilitate application of the reagents to appropriate areas on the intervertebral discs or knee meniscus or adjacent cartilaginous, bony, capsular or ligamentous tissues. This aspect of the present invention is used in a conservative approach to prevent ongoing tearing and degeneration of these tissues and in the case of the intervertebral disc, to prevent subsequent herniations of the disc.

In a third embodiment, the present invention relates to methods and devices for the treatment of intervertebral discs subsequent to or in combination with a nucleus replacement or nucleus augmentation type procedure, and to prevention of extrusion or expulsion of the implanted materials and/or devices. Nucleus pulposus replacement or augmentation technologies rely on the integrity of a surgically weakened annulus fibrosus to prevent migration and extrusion or expulsion of implanted materials or devices. The present invention could be used for resisting annulus tearing after or at the same time of implantation of a nucleus augmentation or nucleus replacement devices. The present invention provides methods and devices such that an injectable nucleus replacement or augmentation materials could be combined with crosslinking reagents to prevent extrusion of the implanted materials. This embodiment would involve delivery of the crosslinking reagents to the central region of the disc and would create an inside-out progression of crosslinking, with the more central annulus tissues being in direct contact with the crosslinking reagents. Alternatively, the present invention provides for a separate crosslinking treatment of the annulus performed at approximately the same time as a nucleus replacement or augmentation procedure. Alternatively, the present invention provides for a crosslinking treatment of the annulus performed subsequent to a nucleus replacement or augmentation procedure. Also, this invention provides for the treatment of the annulus preceding the implantation of the nucleus materials or devices.

In this embodiment, an effective amount of crosslinking reagent is an amount that creates crosslinks in the target tissue, preferably on all of the annulus surrounding a nucleus replacement implant material or device, also preferably on the region surrounding the defect formed by surgical introduction of the implant, also preferably on the surrounding tissues including the cartilaginous vertebral endplates and capsular and ligamentous tissues, such that the annulus resistance to tearing is increased.

Preferably, a method according to this embodiment uses a minimally invasive delivery of the non-cytotoxic crosslinking reagents. A minimally invasive delivery includes a series of injections, to the target tissues of or adjacent to discs which have received or are receiving or will receive, a nucleus replacement or augmentation procedure, in order to contact the appropriate tissue with appropriate concentrations of non-toxic crosslinking reagents. This aspect of the present invention is used in a conservative approach to prevent further tearing of the annulus prior to or following implantation of a nucleus replacement device or materials, and to prevent migration or expulsion or extrusion of implant materials or devices.

Another minimally invasive delivery includes placement of a time-release delivery system such as an, imbedded pellet or time release capsule, or a treated membrane or patch directly into or onto the target tissue. Additional, guidable, arthroscopic-types of devices may be developed to facilitate application of the reagents to appropriate areas on the intervertebral discs or adjacent cartilaginous, bony, capsular or ligamentous tissues. This aspect of the present invention is used in a conservative approach to prevent further tearing of the annulus prior to or following implantation of a nucleus replacement device or materials, and to prevent migration or expulsion or extrusion of implant materials or devices.

A fourth embodiment of the present invention provides methods and devices for enhancing the body's own efforts to stabilize discs in scoliotic spines or other mechanically insufficient or potentially deforming or deforming spines such as listhetic spines, (which contains at least one partially slipped disc), those following a neural decompression procedure such as a laminectomy or subsequent to installation of spinal instrumentation, by increasing collagen crosslinks. A form of mechanical degradation to intervertebral discs occurs as a part of progressive curvature of the spine. For example, spinal curve progression in scoliosis involves increased unloaded curvature of segments of the spine. With this increased curvature there is an associated increase of gravity-induced bending moments on the spine, acting to increase the curvature of these already affected joints. Although it may also be considered as a sustained or static type of load, with a period of loading equal to the period of upright activity during any given day, the "repetitive" or fatigue loading associated with scoliosis curve progression would be comprised of the daily gravitational loads and passive and active muscle and connective tissue actuated loads and their effective moments applied to the spinal column over the course of many days. With increasing deformity, the deforming moments are increased as the "moment arm"—the distance through which the applied forces generate moments—increases. The fundamental rationale behind scoliotic bracing, and bracing for other spinal deformities is to resist these deforming forces and moments, affecting the loading environment of the cells in the bones and connective tissue, and to resist curve progression. The present invention could be used in a conservative approach to prevent ongoing curvature of spines and as an adjunct to corrective surgery to stabilize the remaining discs against loss of correction. It could be used alone or with external bracing.

One aspect of this embodiment provides a method of improving the stability of intervertebral disc tissue in scoliotic or other mechanically insufficient or potentially deforming or defaming spines, such as spondilolisthesis ("slipped discs"), aiding the cell's efforts to increase collagen crosslinks on the tensile (convex) side of the curves and slips, by contacting the tissue with one or more of the non-toxic crosslinking reagents.

In this embodiment, an effective amount of crosslinking reagent is an amount that creates crosslinks in the target tissue, preferably on the convex side of discs at or near the apex or apexes of a spinal curve or of a potential spinal curve, such that at least one of the following effects are achieved: deformity-increasing bending hysteresis is decreased, elastic energy storage and return is increased, and the deformity-increasing bending stiffness is increased.

Preferably, a method according to this embodiment uses a minimally invasive delivery of the non-cytotoxic crosslinking reagents, such as a series of injections, to the tensile (convex) sides of affected discs and adjacent bones, capsular or ligamentous tissues in order to contact the appropriate tissue with appropriate concentrations of non-toxic crosslinking reagents. The appropriate locations for injection are determined using three-dimensional reconstructions of the affected tissues as is possible existing technology, and combining these reconstructions with an algorithm to recommend the optimum placement of these reagents so as to affect the greatest possible restraint of ongoing spinal curve progression. These three-dimensional depictions of preferred locations for crosslinker application may best be created with custom computer software that incorporates medical images of the patient, and are preferably displayed on a computer driven display device such as a lap-top computer or a devoted device. This aspect of the present invention is used in a conservative approach to prevent ongoing curvature of scoliotic and other progressively deforming spines and as an adjunct to corrective surgery to stabilize the remaining discs against loss of correction. It is used alone or with external bracing.

Preferably, a treatment method according to this embodiment incorporates a means for minimally invasive delivery of the non-cytotoxic crosslinking reagent such as placement of a time-release delivery system such as an imbedded pellet or time release capsule, or a treated membrane or patch directly into or onto the target tissue. Additional, guidable, arthroscopic-types of devices may be developed to facilitate application of the reagents to appropriate areas on the intervertebral discs or adjacent bony, capsular or ligamentous tissues. This aspect of the present invention is used in a conservative approach to prevent ongoing curvature of spines and as an adjunct to corrective surgery to stabilize the remaining discs against loss of correction. It is used alone or with external bracing.

Decreased diffusion into the central portion of the intervertebral disc is strongly related to the loss of cell function in the disc and disc degeneration. This loss of diffusion capabilities affects both the cartilaginous endplates of the disc (above and below) and the outer region of the disc, the annulus fibrosus. A fifth embodiment of the present invention provides methods and devices for increasing load supporting collagenous tissue permeability and the flow of nutrition by increasing collagen crosslinks by using one or more of the crosslinking reagents. The present invention increases changes in the hydration of various regions of an intervertebral disc in a way that demonstrates an increased fluid flow into and out of the central region, or nucleus pulposus, of the intervertebral disc afforded by increased crosslinking of the outer region of the disc, the annulus fibrosus and/or the cartilaginous endplates. The changes effected by crosslinking increase the hydraulic permeability of the outer regions of the disc and increase solute transport to and from the central regions of the disc. Also, the present invention increases hydraulic permeability of the outer regions of the knee meniscus tissues and increases solute transport to and from the inner regions of the knee meniscus.

One aspect of this embodiment provides a method to increase the permeability of the outer region of the intervertebral disc, the annulus fibrosus and/or the cartilaginous endplates, and by this improve the fluid flux to and from the central region, or nucleus pulposus, of an intervertebral disc by increasing collagen crosslinks.

A second aspect of this embodiment provides a method to increase the outer disc permeability and increase fluid flux to the central region of the disc to increase the flow of nutrients to the cells in the central region, while also increasing the flow of cell waste products and degraded matrix molecules from the central region of the disc, by increasing collagen crosslinks.

A third aspect of this embodiment provides a method to increase the biological viability of cells or the effectiveness of cell stimulating agents such as cytokines and growth factors in the central region of the intervertebral disc by increasing collagen crosslinks.

This embodiment provides a method for improving flow of nutrients to the central region of the intervertebral disc while also improving outflow of waste products from this central region. This improvement of flow is brought about by increased permeability of the outer region of the disc produced by application of crosslinking reagents to this outer region. This embodiment also provides a method for improving flow of nutrients to the central region of the knee meniscus while also improving outflow of waste products from this central region.

Methods according to this embodiment use a minimally invasive delivery of the non-cytotoxic crosslinking reagents, such as a series of injections, or the placement of a time-release delivery system such as an imbedded pellet or time release capsule, or a treated membrane or patch directly into or onto the target tissue. Additional, guidable, arthroscopic-types of devices may be developed to facilitate application of the reagents to appropriate target areas. These delivery methods are used in a conservative approach to increase the fluid flow, solute transport, nutrient supply, and waste removal to the central region of the disc or meniscus by crosslinking treatment of the outer region, or annulus of the disc or meniscus. These delivery methods function as an essential adjunct to tissue engineering treatments of the intervertebral disc to improve the viability of the implanted or otherwise treated cells and to effect an increase in the biological activity of the disc or meniscus. Tissue engineering treatments and cell or cytokine based methods may include any of the following: implantation of stem cells of any derivation (autogenous or autologous, embryonic or non-embryonic, muscle derived, adipose derived, etc.), gene-therapy delivery of growth factors, implantation of matrices with attached growth factors, direct application of growth factors, implantation of transplanted tissues or cells, implantation of xenograft tissues or cells, to promote increased biological activity in the disc or meniscus. In addition, these delivery methods will be used where no tissue engineering type of treatment is applied with the aim to increase diffusion to the central region of the disc, the nucleus pulposus, or to the central region of the knee meniscus.

It should be noted that the methods and compositions treated herein are not required to permanently improve the resistance of collagenous tissues in the human body to mechanical degradation, or to permanently increase resistance to tissue tearing, or to permanently increase tissue permeability, or to permanently increase resistance to deformity. Assuming that a person experiences 2 to 20 upright, forward flexion bends per day, the increased resistance to fatigue, deformity and tearing and the increase in permeability associated with contact of the collagenous tissue with the crosslinking reagent, may, over the course of time, decrease. Preferably, however, the increased resistance to fatigue, deformity and tearing and the increased permeability lasts for a period of several months to several years without physiologic mechanical degradation. Under such circumstance, the described treatment can be repeated at the time periods sufficient to maintain an increased resistance to fatigue, deformity and tearing and increased permeability. Using the assumption identified above, the contacting may be repeated periodically to maintain the increased resistance to fatigue, deformity and tearing and increased permeability. For some treatment, the time between contacting is estimated to correspond to approximately 1 year for some individuals. Therefore, with either a single treatment or with repeated injections/treatments, the method of the present invention minimizes mechanical degradation of the collagenous tissue over an extended period of time.

Another aspect of the present invention relates to using the aforementioned crosslinking agents as a device or "reagent and application tray" for improving the stabilization of intervertebral discs, for improving the resistance of collagenous tissue to mechanical degradation, for increasing the permeability of the intervertebral disc, for improving the fluid flux to and from the intervertebral disc, and for increasing the biological viability of cells in the intervertebral disc.

The "reagent and application tray" is sterile and contained within a sterile package. An of the necessary and appropriate and pre-measured reagents, solvents and disposable delivery devices are packaged together in an external package that contains a suitable wrapped sterile "reagent and application tray". This sterile tray containing the reagents, solvents, and delivery devices is contained in a plastic enclosure that is sterile on the inside surface. This tray will be made available separate from the computer hardware and software package needed to suggest appropriate application positions.

EXAMPLES 1 AND 2

Thirty-three lumbar intervertebral joints were obtained from ten four-month-old calf spines. The intervertebral joints were arbitrarily divided into 3 groups: untreated controls—12 specimens. Genipin treatment 1 (G1)—6 specimens, and Genipin treatment 2 (G2)—13 specimens. The G1 treatment involved 72 hours of soaking the whole specimen in PBS with a 0.033% concentration of Genipin. Similarly the G2 treatment involved 72 hours of soaking whole specimens in PBS with 0.33% concentration of Genipin. 0.33% Genipin in PBS is produced by dilution of 50 ml of 10.times. PBS (Phosphate Buffered Saline) with distilled water by a factor of 10 to give 500 ml (500 gm) of PBS and mixing in 1.65 grains of genipin to produce the 0.33% (wt %, gm/gm) solution. Previous testing with pericardium and tendon tissue samples demonstrated the reduction of tissue swelling (osmotic influx of water into the tissue) resulting from crosslinking the tissue. Some controls were not subjected to soaking prior to fatigue testing. Others were soaked in a saline solution for 72 hours. Water mass loss experiments were conducted to establish the equivalency of outer annulus hydration between the genipin soaked and 0.9% saline soaked controls. The selection of treatments was randomized by spine and level. The vertebral ends of the specimens were then potted in polyurethane to facilitate mechanical testing.

Indentation testing and compression/flexion fatigue cycling were carried out in the sequence presented in Table 1.

TABLE 1

Experimental protocol

| Measurement Sequence | Measurement | Location |
|---|---|---|
| 1 | Stress Relaxation | Center of the Posterior Annulus |
| 2 | Hardness | Center of the Posterior Annulus |
| | 3000 Compression/Flexion Fatigue Cycles | |
| 3 | Stress Relaxation | 4 mm Lateral to Center |
| 4 | Hardness | Center of the Posterior Annulus |
| | Additional 3000 Compression/Flexion Fatigue cycles | |
| 5 | Stress Relaxation | 4 mm Lateral to Center |
| 6 | Hardness | Center of the Posterior Annulus |

At the prescribed points in the loading regimen, indentation testing was used to find viscoelastic properties as follows. Stress relaxation data was gathered by ramp loading the 3 mm diameter hemi-spherical indenter to 10 N and subsequently holding that displacement for 60 s, while recording the resulting decrease in stress, referred to as the stress relaxation. Indentation testing was also utilized to determine elastic-plastic properties by calculating a hardness index (resistance to indentation) from ramp loading data. Prior to recording hardness measurements, the tissue is repeatedly indented 10 times (60 s/cycle, to the displacement at an initial 10 N load).

This test protocol is based on two principles. First, viscoelastic effects asymptotically decrease with repeated loading. Secondly, hardness measurements are sensitive to the loading history of the tissue. However this effect becomes negligible following 10 loading cycles. In order to minimize these effects, viscoelastic data (stress relaxation) was collected from tissue that had not previously been indented. Alternately, elastic-plastic data (hardness) was collected from tissue that had been repeatedly loaded (preconditioned). In this case, repetitive indentation was intended to reduce the undesired effects of the changing viscoelastic properties, namely lack of repeatability, on hardness measurements. These testing procedures were derived from several preliminary experiments on the repeatability of the measurements with variations of loading history and location.

Following initial indentation testing, the specimen was loaded repetitively in flexion-compression at 200 N for 3000 cycles at a rate of 0.25 Hz. The load was applied perpendicularly to the transverse plane, 40 mm anterior to the mid-point of the specimen in the transverse plane. A second set of indentation testing data is then collected following fatigue cycling. This procedure was followed for two fatigue loading cycles. During all testing, the specimens were wrapped in saline wetted gauze to maintain their moisture content. Fatigue cycling and non-destructive indentation testing were carried out on an MTS 858.02 biaxial, table-top, 10 kN capacity servo-hydraulic materials test station (MTS, Eden Prairie, Minn.), with the MTS Test Star data acquisition system. Several statistical measures were calculated to evaluate the significance of the results. A nested two-way analysis of variance (ANOVA) was utilized to confirm effects due to treatment and number of fatigue cycles. Due to the non-parametric nature of the data, the Mann-Whitney non-parametric rank-sum test was used to assess the null hypotheses that the treatment did not affect: 1) the pre-cycling mechanical parameters of the tissue, or 2) the amount of change (degradation) in elastic-plastic and viscoelastic mechanical parameters due to fatigue loading. The confidence level for statistical significance was set at $p<0.05$.

Nested two-way ANOVA analysis determined that both viscoelastic (relaxation) and elastic-plastic (hardness) mechanical parameters were independently affected by fatigue cycling and by treatment type. These statistical results are presented in Table 2.

The relaxation test results are presented graphically in FIG. 1.

There was an initial shill downward of the relaxation curve caused by the crosslinking treatment. This would represent a beneficial effect as higher stress relaxation would be associated with more severely degraded tissue (Lee 1989). The initial pre-Fatigue relaxation of the G1 and G2 treatment groups were 26% and 19% less than ($p=0.009$ and $p=0.026$) the pre-fatigue relaxation of the controls respectively. There was also dramatic improvement in fatigue resistance as demonstrated by the change in relaxation after 6000 non-traumatic loading cycles. The change in relaxation due to 6000 fatigue cycles for the G2 treated discs was less than a third of the change in the controls ($p=0.044$). However, the lesser concentration of Genepin did not bring about the same improvement in fatigue resistance.

Figure 2:
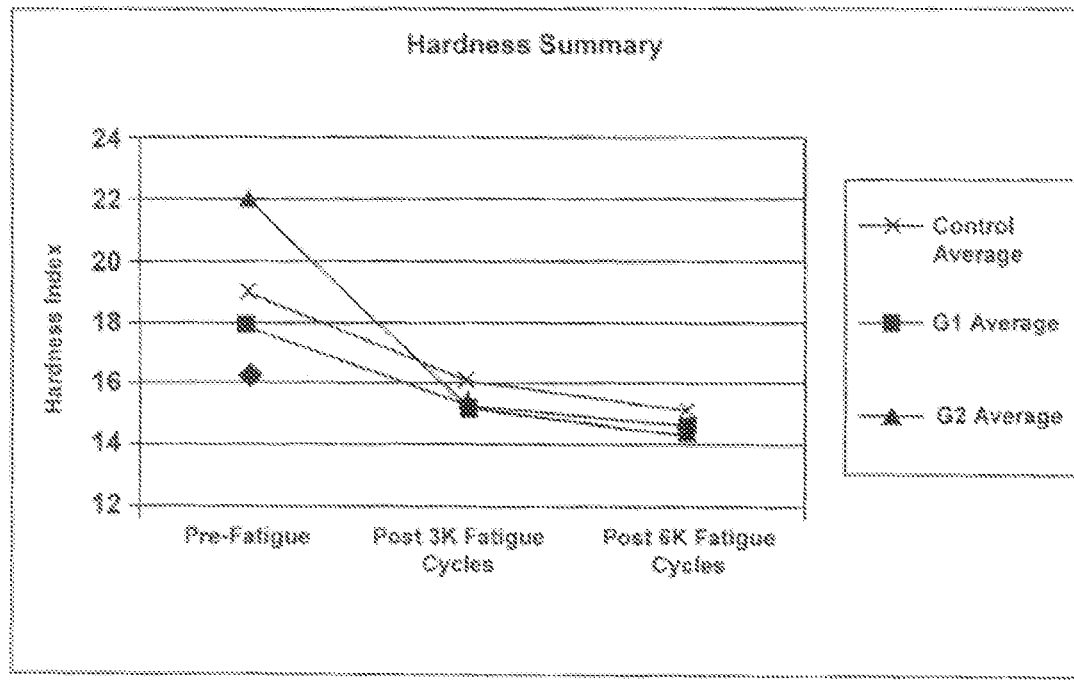
FIG. 2 is a graph of Brinnell's hardness index v. numbers of cycles showing the effect of genipin crosslinking treatments (G1=0.033 g/mol, G2=0.33 g/mol) on posterior intervertebral disc hardness or resistance to penetration.

The hardness test results are presented graphically in FIG. 2. There is an initial shift upward of the hardness data caused by the G2 crosslinking treatment. This would represent a beneficial effect as loss of hardness would signal a loss of structural integrity in the tissue. The initial pre-fatigue hardness of the G2 treatment group was 17% greater than that of the control group ($p=0.026$). However this beneficial effect appears to have eroded prior to 3000 fatigue cycles and the change in hardness between 3000 and 6000 cycles is essentially the same for the two groups (G2=−0.94, Control=−1.01).

TABLE 2

Results of nested two-way ANOVA analysis

| Material Properly | Factor | F-Value | Probability |
| --- | --- | --- | --- |
| Stress Relaxation | Treatment | 16.060 | 1.085E−06 |
| | Fatigue Cycling | 9.676 | 2.500E−03 |
| | Interaction | 1.402 | 2.515E−01 |
| Hardness | Treatment | 20.023 | 6.405E−08 |
| | Fatigue Cycling | 5.898 | 1.710E−02 |
| | Interaction | 4.228 | 1.760E−02 |

The data presented above quantifies the elastic and viscoelastic mechanical degradation of intervertebral disc tissue due to repetitive, non-traumatic loading. The results of these experiments establish that non-toxic crosslinking reagents reduce the fatigue-related degradation of material properties in a collagenous tissue—namely the intervertebral disc. More than a three-fold reduction in viscoelastic degradation was brought about by soaking the calf disc tissue in 0.33 g/mol concentration of genipin. The tested formulation was unable to sustain an improvement in the elastic mechanical properties (hardness) to 3000 test cycles.

Accurately estimating the length of time it would take an average person to experience a comparable amount of wear and tear on their spinal discs is difficult. Certainly, in addition to the mechanical degradation imposed by the described testing, there is the added—"natural"—degradation of these dead tissues due to the testing environment. The non-loaded controls showed this "natural" degradation of material properties to be insignificant. Measures were taken to minimize this natural degradation by keeping the specimens moist throughout the testing and by accelerating the loading frequency. At the same time, loading frequency was kept within physiologic limits to prevent tissue overheating. It should be noted that these measures constitute standard protocol for in vitro mechanical testing of cadaveric tissues. Assuming that a person experiences 2 to 20 upright, forward flexion bends per day, these data roughly correspond to several months to several years of physiologic mechanical degradation.

The described treatment could be repeated at the time periods represented by, for instance, 3000 fatigue cycles at this load magnitude. Using the assumption identified above, this number of cycles may be estimated to correspond to approximately 1 year for some individuals. Therefore, with either a single treatment or with repeated injections/treatments, an individual may be able to minimize mechanical degradation of their intervertebral discs over an extended period of time. Another option would involve a time-release delivery system such as a directly applied treated patch, a eel or ointment.

EXAMPLES 3 AND 3A

Experiments were conducted to evaluate the efficacy of applying different formulations of crosslinking reagents with known minimal cytotoxicity unilaterally to intervertebral disc annular tissue in order to affect the lateral bending stability of the tissue compared to pre-treatment.

Experiments utilized 5 calf spine segments, each segment comprised of 3 lumbar intervertebral joints (motion segments), four vertebrae and the intervening 3 discs. The pedicles were cut and the posterior processes removed. The segments were randomly divided into a 0.33% by weight genipin crosslinked group, a 0.5% genipin group, a 0.66% genipin group, and a 0.66% genipin plus 0.1% proanthocyanidin group. Each group consisted of one 3 motion segment specimen. Each pre-treated spine served as its own control. Repeated testing was performed on some untreated and treated specimens to determine repeatability of the measurements. Additional appropriate concentrations and combinations of known minimally cytotoxic crosslinking reagents will be chosen based on the documented cytotoxicity of a particular tissue. In this regard it is expected that sugar solutions (such as ribose and l-threose), byproducts of metabolism (such as methylglyoxal and glyoxal) and naturally occurring enzymes (such as lysyl oxidase and transglutaminase) will be essentially non-cytotoxic. Similar testing will be conducted on fresh-non-frozen animal tissue with appropriate sterilization procedures and antibiotics to prevent tissue degradation. Sugar solutions will be injected unilaterally into fresh intervertebral discs to induce non-enzymatic glycation crosslinks over a period of sterile incubation.

Four-point lateral bending tests were conducted using an MTS 858 materials testing system with custom fixtures while load and displacement were recorded digitally. First the specimens were cleaned of muscle and other non-load supporting tissues, and then the terminal vertebrae were potted in polyurethane to half their height in square molds. The potted spine segments are then placed on the bottom 2 rollers such that the lateral sides of the spines were positioned in a vertical plane. The bending load was actuated by 2 upper rollers in contact with the central two vertebrae of the segment. Care was taken to ensure that the pre, and post-treatment positioning of the specimens on the rollers was similar. As an attribute of 4-point bending, the central region of the test specimen, including the central disc between the 2 upper rollers, has an evenly distributed shear load and bending moment. A ramp load to 100 N (0.5 mm/s) was applied in right and left lateral bending to each spine both prior to treatment and after crosslinking treatment.

The crosslinking reagents were delivered to each of the discs in each spine specimen by 2 to 3 injections into one lateral side of the spine. Each injection was comprised of 1 cc of reagent. A 26 gauge hypodermic needle was used. The treated segments were allowed to sit in a closed container wrapped in moist paper towels for 36 hours prior to final testing. After testing, the discs were cut transversely to visually document the region of the tissue contacted by the reagents.

Resistance to lateral bending and lateral bending stability were assessed by two measures, one elastic-plastic, the other viscoelastic. The first was the neutral zone (low-load) bending stiffness evidenced by the amount of deformation from 0.1 to 100 N of deforming force. The second was the hysteresis or bending energy lost or not stored by the tissues. Less hysteresis, or a lower percentage of hysteresis compared to strain energy or the amount of bending energy stored and returned, corresponds to greater capacity to bounce back from a bend rather than remain in the deformed position. It also reflects a more elastic, spring-like response as compared to a more viscous response.

The injections effectively distributed the crosslinking reagents to approximately one-half of the disc annulus, right or tell hall. See Table 3. The neutral zone bending stiffness was consistently increased by treatment only when the treated side was in tension. The average magnitude of stiffness increase was 12% with a 26% increase in the case of 0.66% genipin plus 0.1% proanthocyanidin treatment. The hysteresis was consistently decreased by treatment only when the treated side was in tension. The average decrease in hysteresis was 31% with a 37% decrease in the case of 0.66% genipin plus 0.1% proanthocyanidin treatment.

These results demonstrate that crosslink augmentation with minimally non-toxic crosslinking reagents effectively reduces instability of intervertebral discs toward deforming forces as is expected in scoliotic spines. The stabilizing effect was observed to be greater with the 0.66% genipin plus 0.1% proanthocyanidin treatment. Consequently, by reducing the viscoelastic dissipation of bending energy and increasing the bounce-back of the discs (lowered hysteresis) and by increasing the bending stiffness in the direction that puts the treated side of the spine in tension, injectable non-toxic crosslink augmentation effectively resists scoliotic curve progression as well as other progressive spinal deformities.

EXAMPLE 4

By measuring the change in hydration of different regions of the intervertebral disc (nucleus pulposus, inner annulus, and outer annulus fibrosus) prior to and after periods of soaking, sustained compressive loading, and resoaking, the fluid flux to and from different regions can be determined. By comparing these measurements between control discs and discs treated with crosslinking reagents known to have minimal cytotoxicity, we see the effect of crosslinking treatment on fluid flux and permeability.

A total of 24 calf (4 month old bovine) intervertebral discs were used for this study. Water content of three different areas of the discal tissue were tested—the nucleus pulposus, inner annulus fibrosus and outer annulus fibrosus. Hydration change was determined by weighing the specimen using a micro-balance (sensitivity: 0.1 mg). Water content (M) was calculated as:

$$M = (\text{Wet Weight} - \text{Dry Weight})/\text{Wet Weight} = g\ H2O/g\ \text{Wet Weight}$$

The drying procedure consisted of putting the specimens in the oven with a controlled temperature of 90.degree C. for 24 hours.

The specimens were separated into four tests:

1. Group A: Three specimens were in this group. It served as a control group. The specimens were soaked in PBS (phosphate buffered saline) for 1 day and then the hydration analysis was performed.

TABLE 3

| Specimen # Side Up | Treatment | Side Treated | Hysteresis | Max Displacement | Max Load | Loss of Hysteresis | Change in Stiffness: Compression side | Change in Stiffness: Tension on side |
|---|---|---|---|---|---|---|---|---|
| 1L | Control | | 87.21 | 6.878 | 99.7 | | | |
| 1L | 0.50G | L | 97.47 | 8.381 | 99.0 | | −22% | |
| 1R | Control | | 170.73 | 8.860 | 98.7 | | | |
| 1R | 0.50G | L | 92.91 | 8.822 | 96.6 | 46% | | 0.43% |
| 2L | Control | | 64.41 | 3.463 | 99.3 | | | |
| 2L | 0.50G | L | 47.80 | 3.873 | 97.6 | | −12% | |
| 2R | Control | | 47.76 | 3.884 | 98.3 | | | |
| 2R | 0.50G | L | 40.28 | 3.573 | 101.1 | 16% | | 8% |
| 3L | Control | | 80.70 | 7.116 | 100.4 | | | |
| 3L | 0.33G | L | 58.79 | 5.041 | 99.7 | | 29% | |
| 3R | Control | | 78.52 | 5.951 | 100.0 | | | |
| 3R | 0.33G | L | 50.67 | 4.924 | 97.6 | 35% | | 17% |
| 4L | Control | | 61.97 | 5.62 | 101.1 | | | |
| 4L | 0.66G | | 49.88 | 5.259 | 99.3 | 20% | | 6% |
| 4R | Control | | 63.65 | 5.359 | 98.7 | | | |
| 4R | 0.66G | | 50.92 | 4.931 | 99.3 | | 8% | |
| 5L | Control | | 41.58 | 3.511 | 100.7 | | | |
| 5L | 0.66G + 0.1PA | | 49.87 | 4.049 | 101.4 | | −15% | |
| 5R | Control | | 74.89 | 4.683 | 100.4 | | | |
| 5R | 0.66G + 0.1PA | | 47.08 | 3.460 | 100.4 | 37% | | 26% |
| Average | | | | | | 31% | −2% | 12% |

2. Group B1: Four specimens were in this group. In addition to the one day PBS soaking, the specimens soaked in PBS for 2 more days as a control and then the hydration analysis was performed.

Group B2: Five specimens were in this group. In addition to the one day PBS soaking, the specimens were soaked in 0.33% genipin solution for 2 days and then the hydration analysis was performed.

3. In group C, a small daytime amount of constant compressive loading (creep) was simulated.

C1: Three specimens were in this group. The specimens were soaked in PBS for 3 days and then 750N of compression was applied by a materials testing machine for 1 hour. The disc was compressed in a 5 degree of flexion posture produced by two rollers attached to the loading ram of the materials testing machine. The hydration analysis was performed immediately after the creep loading.

C2: Three specimens were in this group. The specimens were soaked in 0.33% Genipin solution for 2 days after 1 day of PBS soaking and performed identical creep loading with 750N compressive load. The hydration analysis was performed immediately after the creep loading.

4. In group D, the imbibition of water following a period of compressive loading that typically occurs in the night time as a person is in a recumbent posture was simulated.

D1: The specimens were soaked in PBS solution for 3 days and then 1 hour of creep loading at 750 N was applied. After the creep loading, the specimens were placed in a container in 1 PBS for one more day followed by the hydration analysis.

D2: Three specimens were included and were soaked in 0.33% genipin solution for 2 days after one day of PBS soaking. A creep load of 750N for one hour was then applied. The specimens were put in PBS for another day followed by the hydration analysis.

See Table 4. In general, creep loading expels fluid out of the tissues and after creep re-absorption of fluid occurs. The result pertinent to the present invention was that there was a combined 64% increased fluid flow into and out of the central nucleus region in the genipin crosslinking reagent treated discs compared to controls.

dicular to the travel of a metal cylinder placed in a pre-existing radial cut. The cylinder was then pulled radially (perpendicular to lamellae) towards the external layer. Time dependent force and displacement data was acquired simultaneously. Tearing resistance was quantified in two ways: peak force normalized by specimen thickness and tearing energy per area of tear. Differences between groups were analyzed using the Mann-Whitney non-parametric test.

Normalized peak force was 23.9 and 42.7 N/mm for control and genipin crosslinks groups respectively (p=0.076). Total energy per area of tear was 19.0 and 40.2 mJ/mm^2 for control and genipin groups (p=0.047, FIG. 1).

Crosslink augmentation of the extracellular matrix of the annulus fibrosus was found to approximately double the peak force and the total energy required to propagate a radial tear. Injectable crosslink augmentation of the annulus fibrosus can prevent or slow down the degradation leading to loss of the contents of the disc's central region, whether it involves herniation of nucleus pulposus or expulsion of nucleus replacement devices or materials.

EXAMPLE 6

One can perform a primary, conservative nonsurgical treatment of a patient suffering from back pain and possibly showing MRI or radiographic signs of disc degeneration by injecting an effective amount of crosslinking agent, such as 400 L-Threose in saline (0.15M) or a solution comprised of 200 mM methylglyoxal in saline or a solution of 200 mM glyoxal or a solution 200 mM EDC or a solution comprised of 50-100 µg lysyl oxidase in a 0.1 M urea saline solution or a solution comprised of 50 µg/ml human recombinant transglutaminase in saline, or a solution comprised of 200 µg/ml of purified animal liver transglutaminase in saline, to the affected disc. This treatment can be performed in order to stabilize the degenerated intervertebral joint, to increase the durability (fatigue resistance) and tear resistance of the affected disc tissues, to improve nutritional flow to and waste product flow from the degraded disc, to enable rehydration of the disc and a subsequent increase in disc height, to change the load trans-

TABLE 4

|  | Gr B1 | Gr B2 | Gr C1 | Gr C2 | Gr D1 | Gr D2 | Control Flux | Genipin Flux | % increase by Genipin |
|---|---|---|---|---|---|---|---|---|---|
| Inner AF | 0.768771 | 0.762891 | 0.745779 | 0.739397 | 0.808709 | 0.0.816669 | 0.08592 | 0.10077 | 17.3% |
| Outer AF | 0.723259 | 0.726776 | 0.696626 | 0.692404 | 0.720096 | 0.710972 | 0.050010 | 0.05294 | 5.7% |
| NP | 0.834041 | 0.831405 | 0.825998 | 0.816964 | 0.848403 | 0.852357 | 0.03045 | 0.04983 | 63.7% |

These results demonstrate that augmentation of crosslinking of intervertebral disc tissue resulted in an increased fluid flow into and out of the central region of the intervertebral disc. This increased fluid flux to the disc nucleus indicates that this treatment effects an increase of nutrients supplied to cells in the central region of the disc as well as an increased removal of cell and matrix waste products.

EXAMPLE 5

Ten annulus fibrosus circumferentially aliened specimens from bovine lumbar (T12-L5) intervertebral discs were divided into two groups and either soaked two days in a 0.15M PBS or a 0.15M PBS plus 0.33% genipin solution. A custom loading fixture attached to a uniaxial materials testing system was designed to hold an annulus specimen perpenmission through the afflicted disc, to prevent further degenerative changes to the disc, to potentially prevent migration and herniation of disc material with normal load bearing, to potentially relieve pressure on a neural element external to the disc, to potentially relieve pressure on nerve endings in the disc, and to reduce the incidence of back pain episodes. The crosslinking agent injection can be accompanied by standard injections of pain medication or steroids if deemed appropriate by the physician.

EXAMPLE 7

One can treat a patient who has undergone installation of spinal instrumentation to minimize consequent deformities or adjacent segment degeneration by treating the whole or part of the adjacent intervertebral disc with a crosslinking agent, such as 400 L-Threose in saline (0.15M) or a solution comprised of 200 mM methylglyoxal in saline or a solution of 200 mM glyoxal or a solution 200 mM EDC or a solution comprised of 50-100 µg lysyl oxidase in a 0.1 M urea saline solution or a solution comprised of 50 µg/ml human recombinant transglutaminase in saline, or a solution comprised of 200 µg/ml of purified animal liver transglutaminase in saline. Immediately after installation of surgical apparatus or within a few days after surgery the crosslinking agent can be injected into the whole disc adjacent to the instrumented levels. Fluoroscopic or other imaging means can be used to deliver the crosslinking agent to the selected tissues. In the case of a long, multilevel thoracolumbar stabilization, the inferiorly adjacent (caudal) lumbar disc can be treated to prevent loss of natural lordosis, and the superiorly adjacent (towards the head). In the case of a single or multi-level fusion or non-fusion (such as artificial disc implantation or dynamic stabilization) the adjacent disc levels can be treated to prevent accelerated intervertebral joint degeneration (adjacent disc syndrome) at that level.

EXAMPLE 8

If a patient is suffering from grade 1 spondylolisthesis (25% or less slip of one vertebra relative to an adjacent vertebra), neurological problems including pain or weakness in the legs, or back pain, where conventional surgical options may dictate performing a laminectomy to decompress the neural structures, one can treat the patient with the same laminectomy procedure combined with injections of a crosslinking reagent, such as 400 mM L-Threose in saline (0.15M) or a solution comprised of 200 mM methylglyoxal in saline or a solution of 200 mM glyoxal or a solution 200 mM EDC or a solution comprised of 50-100 µg lysyl oxidase in a 0.1 M urea saline solution or a solution comprised of 50 µg/ml human recombinant transglutaminase in saline, or a solution comprised of 200 µg/ml of purified animal liver transglutaminase in saline, into the partially "slipped" disc, either to the posterior aspect of the disc or to the entire annulus to minimize consequent progression of the deformity. In such a case, prior to, at the same time, or subsequent to the decompression procedure (laminectomy), according to the preference of the physician administering the treatment, multiple injections of a preferred, non-toxic crosslinking agent can be performed through a single or multiple injection sites. The patient should be instructed to avoid strenuous activities for a period of a few days. The internal stabilization afforded by the crosslinking treatment can be augmented by other conservative measures such as external bracing according to the physician's judgment. If administered prior to any decompression procedure, the crosslinking treatment can provide stability to the spine in the region of the slipped disc thus potentially avoiding the need for surgery including surgical decompression.

EXAMPLE 9

This is an example of in vivo animal testing of a hybrid treatment including implantation of autologous stem cells and crosslinking treatment. Muscle cell derived autologous stem cells can be injected into the nucleus of mechanically degraded rat-tail intervertebral discs of four groups of Sprague-Dawley rats. One of the groups can have an effective non-toxic crosslinking reagent such as 400 mM L-Threose in saline (0.15M) or a solution comprised of 200 mM methylglyoxal in saline or a solution of 200 mM glyoxal or a solution 200 mM EDC or a solution comprised of 50-100 µg lysyl oxidase in a 0.1 M urea saline solution or a solution comprised of 50 µg/ml human recombinant transglutaminase in saline, or a solution comprised of 200 µg/ml of purified animal liver transglutaminase in saline, injected into the target discs prior to implantation of the stem cells. Another group can have the crosslinking reagent injected into the target discs at approximately the same time that the stem cells are implanted. A third group can have the target discs treated with crosslinking 1 day following implantation of the stem cells. The fourth group can have the stem cells implanted with no accompanying crosslinking treatment. Prior to treatment, each candidate disc can receive 1 to 2 weeks of repetitive mechanical loading (compression bending to 1.2 MPa) to degrade the discs as documented by prior experiments. Following treatment the rats can be maintained for an additional 2, 4, 8, or 16 weeks prior to sacrifice. Subsequent to sacrifice histochemical (quantify collagen I/II & proteoglycan matrix content, apoptotic cells, and inflammatory cells), mechanical, anabolic (Real-time PCR analysis will quantify collagen-1a1, collagen-2a1 and aggregan expression) and catabolic (MMP-3, MMP-13, ADAMTs-4 mRNA markers) assays can be performed on the disc tissue to document and quantify the efficacy, viability and duration of the cell-based treatment technique for the crosslinked and noncrosslinked groups over the 4 time periods. Crosslink augmentation of the disc should improve stem cell viability and duration of effects, regeneration and repair of degraded extracellular tissues, disc viscoelastic and elastic-plastic material properties, and joint stability.

EXAMPLE 10

One can treat a patient who has undergone, or will undergo, a cell or cytokine (growth factor) based treatment of a degenerated disc (including but not limited to implantation of stem cells of any derivation, gene-therapy delivery of growth factors, implantation of matrices with attached growth factors, direct application of growth factors, implantation of transplanted tissues or cells, implantation of xenograft tissues or cells) with an adjunct treatment of the disc (preferably including endplates and annulus) by injecting a crosslinking agent, such as 400 mM L-Threose in saline (0.15M) or a solution comprised of 200 mM methylglyoxal in saline or a solution of 200 mM glyoxal or a solution 200 mM EDC or a solution comprised of 50-100 µg lysyl oxidase in a 0.1 M urea saline solution or a solution comprised of 50 µg/ml human recombinant transglutaminase in saline, or a solution comprised of 200 µg/ml of purified animal liver transglutaminase in saline into or adjacent to the targeted areas (one would expect injection of the superior and inferior aspects of the disc nucleus and inner annulus to promote contact between the crosslinking agents and the cartilaginous endplates of the disc). This treatment would be administered in order to affect an increase in nutrient flow to the cells in the disc, to increase waste product removal from the cells, to increase the regenerative and repair capabilities of the cells, and by this to improve the efficacy of the cell or cytokine based treatment, and to improve the viability of cells in the disc, and by this to sustain the augmented biological activity and increase the duration of beneficial activities.

EXAMPLE 11

One can treat a patient who has undergone, or will undergo, a nucleus replacement treatment of a moderately degenerated disc (including but not limited to implantation of nucleus replacement material or device) with an adjunct treatment of the disc (preferably including endplates and annulus) by injecting a crosslinking agent, such as 400 mM L-Threose in saline (0.15M) or a solution comprised of 200 mM methylglyoxal in saline or a solution of 200 mM glyoxal or a solution 200 mM EDC or a solution comprised of 50-100 μg lysyl oxidase in a 0.1 M urea saline solution or a solution comprised of 50 μg/ml human recombinant transglutaminase in saline, or a solution comprised of 200 μg/ml of purified animal liver transglutaminase in saline into all of the remaining disc annulus material and into or adjacent to the cartilaginous endplates of the disc (one would expect injection of the superior and inferior aspects of the disc nucleus region and inner annulus region to promote contact between the crosslinking agents and the cartilaginous endplates of the disc). This treatment would be administered in order to affect an increase in annulus tear resistance and resist fissuring in the annulus and through the cartilaginous endplates, to prevent migration or extrusion or expulsion of implanted materials and devices and by that to improve the efficacy of the nucleus replacement treatment, to maintain the long term integrity of the annulus and disc, to maintain augmented disc height, and by this to reduce compression of neural tissues and to reduce pain for longer duration post treatment.

EXAMPLE 12

This is an example of biomechanical testing of cadaveric intervertebral joints after crosslinking treatment.

Individual calf and human cadaveric thoracolumbar intervertebral joint specimens can be subjected to repetitive combined flexion-compression-anterior shear loading in order to simulate a kyphotic deformity of an intact spinal segment adjacent to a fused or otherwise instrumented segment. Four treatment groups can be compared with untreated controls. Each group contains 5 or more cadaveric specimens from similar regions of thoracolumbar spines. The first treatment group can be treated in the posterior half of the annulus by injections with a solution comprised of 400 mM L-Threose in saline (0.15M). The total volume injected in each disc of this group can be 1 ml.

The second treatment group can be treated across the entire disc by injections with a solution of 400 mM L-Threose in saline. The third treatment group can be treated across the whole disc by injections with a solution comprised of 200 mM methylglyoxal in saline. The fourth treatment group can be treated across the whole disc by injections with a solution comprised of 50-100 μg lysyl oxidase in saline. The total volume injected in these discs can be 3 ml. The preventative effects of the different crosslinking treatments can be compared by evaluating amounts of unrecovered deformation subsequent to crosslink treatment and application of deforming loads. One thousand cycles of combined loading can be applied after which permanent deformation is measured using an optoelectronic position measurement system. Peak loads and moments can be uniform between groups. Peak moment can be between 1 Nm and 3 Nm depending on the spinal level (i.e. upper thoracic being 1 Nm, lumbar being 3 Nm). Peak shear load can be 200 N and peak compressive load can be 500 N in lumbar intervertebral levels. Peak shear can be 100 N and peak compression can be 250 N in upper thoracic levels. The permanent deformation measurements should demonstrate a decreased amount of deformation in the crosslinked specimens on average compared to the untreated discs.

The invention has been described in terms of certain preferred and alternate embodiments which are representative of only some of the various ways in which the basic concepts of the invention may be implemented. Certain modification or variations on the implementation of the inventive concepts which may occur to those of ordinary skill in the art are within the scope of the invention and equivalents, as defined by the accompanying claims.

LIST OF REFERENCES

The following publications are hereby incorporated by reference:

List of References

Boyd-White, J, Williams, J C, Effect of cross-linking on matrix permeability: a model for AGE-modified basement membranes, Diabetes, 45:348-353, 1996.

Bucks alter, J A, Aging and degeneration of the human intervertebral disc, Spine, 20:1307-14, 1995.

Chachra, D, Gratzer, P F, Pereira, C A, Lee, J M, Effect of applied uniaxial stress on rate and mechanical effects of cross-linking in tissue-derived biomaterials, Biomaterials, 17:1865-75, 1996.

Chen, A C, Temple, M M, Ng, D M. Richardson, C D, DeGroot, J. Verzijl, N, teKoppele, J M, Sah, R L. Age-related crosslinking alters tensile properties of articular cartilage, 47.sup.th Annual Meeting. Orthopaedic Research Society. p. 128. 2001.

Duance. V C. Crean. J K G, Sims, T J, Avery, N, Smith, S, Menage, J. Eisenstein, S M, and Roberts, S, Changes in collagen cross-linking in degenerative disc disease and scoliosis, Spine, 23:2545-51, 1998.

Greve, C, Opsahl, W, Reiser, K, Abott, U, Kenney, C, Benson, D, and Rucker, R, Collagen crosslinking and cartilage glycosaminoglycan composition in normal and scoliotic chickens, Biochemica et Biophysica Acta, 967:275-283, 1988.

Horner H A. Urban J P. 2001 Volvo Award Winner in Basic Science Studies: Effect of nutrient supply on the viability of cells from the nucleus pulposus of the intervertebral disc. Spine. 26:2543-9, 2001.

Lee, J M, Haberer, S A, Boughner, D R, The bovine pericardial xenograft: 1. Effect of fixation in aldehydes without constraint on the tensile viscoelastic properties of bovine pericardium, Journal of Biomedical Materials Research, 23:457-475, 1989.

Sung H W. Chang Y. Chiu C T. Chen C N. Liang H C. Mechanical properties of a porcine aortic valve fixed with a naturally occurring crosslinking agent. Biomaterials. 20(19):1759-72. 1999, (a)

Sung, H W, Chang, Y, Chiu, C T, Chen, C N, Liang, H C, Crosslinking characteristics and mechanical properties of a bovine pericardium fixed with a naturally occurring crosslinking agent, Journal Biomed. Materials Res., 47:116-126, 1999, (b)

Thompson, J B, Kindt, J Drake, B. Hansma, H G, Morse, D E, and Hansma, P K, Bone indentation recovery time correlates with bond reforming time, Nature, 414:773-6, 2001.

Wang, X D, Masilamani, N S, Mabrey, J D, Alder, M E, Agrawal, C M, Changes in the fracture toughness of bone may not be reflected in its mineral density, porosity, and tensile properties, Bone, 23:67-72, 1998.

Zeeman R. Dijkstra P J. van Wachem P B, van Luyn M J. Hendriks M. Cahalan P T. Feijen J. Crosslinking and modification of dermal sheep collagen using 1,4-butanediol diglycidyl ether. Journal of Biomedical Materials Research. 46(3):424-33. 1999.

I claim:

1. A method of treatment of native, non-denatured tissue of the annulus fibrosus of an intervertebral disc that is subject to expulsion or extrusion of any implanted device or material that is present for spinal nucleus treatment, comprising the step of:

contacting at least a portion of the tissue with a composition comprising an effective amount of a reagent that increases crosslinks in the tissue, thereby increasing the resistance of the annulus fibrosus to expulsion or extrusion of an implanted device or material.

2. The method of claim 1 in which there is more than one crosslinking reagent.

3. The method of claim 1 in which the reagent is non-toxic.

4. The method of claim 1 in which the composition contains one or more of the following reagent concentrations:
- at least 0.001% (.01mg/ml) of human recombinant transglutaminase;
- at least 0.01% (0.1mg/ml) of purified animal liver transglutaminase:
- at least 0.25% genipin;
- at least 0.1% proanthrocyanidin;
- at least 100 mM EDC;
- at least 50 mM non-enzymatic agent; or
- at least 0.001% lysyl oxidase.

5. The method of claim 4 in Which the reagent is a non-enzymatic reagent.

6. The method of claim 5 in which the composition further comprises an oxidant, a buffer, or a combination thereof.

7. The method of claim 6 in which the oxidant is hydrogen peroxide, sodium perearbonate, sodium borate, an amino acid hydroperoxide, or perborate, and wherein the butler is sodium bicarbonate or phosphate.

8. The method of claim 4 in which the non-enzymatic agent is one or more of the following agent concentrations:
- at least 100 mM ribose
- at least 100 mM L-threose;
- at least 50 mM methylglyoxal; or
- at least 50 mM glyoxal.

9. The method of claim 4 in which the reagent is in a 0.1 M urea solution.

10. The method of claim 4 in which the reagent is in a substantially non-cytotoxic carrier medium.

11. The method of claim 10 in which the pH of the carrier medium is adjusted to be substantially the same as the healthy tissue environment.

12. The method of claim 11 in which the carrier medium is a phosphate buffered saline solution.

13. The method of claim 1 in which the step of contacting at least a portion of the tissue with the reagent is occurs at the same time or prior to or after implantation of a nucleus augmentation or replacement device or material.

* * * * *